United States Patent
Kia

(10) Patent No.: US 9,553,727 B2
(45) Date of Patent: Jan. 24, 2017

(54) SECURE AND MOBILE BIOMETRIC AUTHENTICATION FOR ELECTRONIC HEALTH RECORD MANAGEMENT

(76) Inventor: Omid Ebrahimi Kia, North Bethesda, MD (US)

( * ) Notice: Subject to any disclaimer, the term of this patent is extended or adjusted under 35 U.S.C. 154(b) by 1692 days.

(21) Appl. No.: 13/010,743

(22) Filed: Jan. 20, 2011

(65) Prior Publication Data

US 2011/0178931 A1    Jul. 21, 2011

Related U.S. Application Data

(60) Provisional application No. 61/297,271, filed on Jan. 21, 2010.

(51) Int. Cl.
| | |
|---|---|
| G06F 21/32 | (2013.01) |
| H04L 9/32 | (2006.01) |
| G06Q 10/06 | (2012.01) |
| G06Q 40/08 | (2012.01) |
| G06Q 50/22 | (2012.01) |
| H04L 29/06 | (2006.01) |
| H04W 12/06 | (2009.01) |

(52) U.S. Cl.
CPC ............. *H04L 9/3231* (2013.01); *G06F 21/32* (2013.01); *G06Q 10/06* (2013.01); *G06Q 40/08* (2013.01); *G06Q 50/22* (2013.01); *H04L 63/0861* (2013.01); *H04W 12/06* (2013.01)

(58) Field of Classification Search
USPC ........................................................ 705/50
See application file for complete search history.

(56) References Cited

U.S. PATENT DOCUMENTS

| | | | | |
|---|---|---|---|---|
| 7,181,017 | B1* | 2/2007 | Nagel et al. .................. | 380/282 |
| 2003/0229492 | A1* | 12/2003 | Nolan ..................... | G10L 17/06 704/247 |
| 2006/0180660 | A1* | 8/2006 | Gray ..................... | G06Q 20/24 235/380 |
| 2006/0206724 | A1* | 9/2006 | Schaufele et al. ............ | 713/186 |
| 2008/0091425 | A1* | 4/2008 | Kane ............................ | 704/246 |
| 2008/0172737 | A1* | 7/2008 | Shen ................... | G06F 21/6245 726/21 |
| 2009/0206993 | A1* | 8/2009 | Di Mambro ............ | G06F 21/32 340/5.84 |
| 2011/0185178 | A1* | 7/2011 | Gotthardt ..................... | 713/172 |

* cited by examiner

*Primary Examiner* — John Hayes
*Assistant Examiner* — Jason Fenstermacher
(74) *Attorney, Agent, or Firm* — Esmael Dinan; David G. Grossman

(57) ABSTRACT

A portable device receives an encrypted message from an electronic health record database server including a request to perform a biometric authentication to approve a transaction. The device prompts a user to speak a pass phrase. The device creates a set of variables including the pass phrase and at least one more variable characterizing the spoken voice. The authentication module transmits an encrypted message to the health record database server including a session identification information and the set of variables. In response, the device receives an encrypted message from the health record database server determining whether the biometric authentication is successful and the transaction is approved, wherein determination is made by the health record database server and is based on verifying the session identification information, the pass phrase, and the user identity.

9 Claims, 7 Drawing Sheets

SECURE AND MOBILE BIOMETRIC AUTHENTICATION FOR ELECTRONIC HEALTH RECORD MANAGEMENT

CROSS-REFERENCE TO RELATED APPLICATIONS

This application claims the benefit of U.S. Provisional Application No. 61/297,271, filed Jan. 21, 2010, entitled "Secure and Mobile Intelligent Biometric Authentication for Intelligent Health Record Management," which is hereby incorporated by reference in its entirety.

FIELD OF THE INVENTION

The present invention is in the technical field of record management. More particularly, the present invention is related to secure health record management; where the health record information transactions are authenticated using the user's biometrics characteristics via a portable device.

BACKGROUND OF THE INVENTION

Patient's privacy and confidentiality of personal information is taken very seriously. Most caregivers strictly follow redundancy and compliance to try to be legal, with mixed results. In today's health care system one of the backbones of the industry seems to still use paper. Paper is used to write patient demographics, insurance and the responsible adult for the first time visitors. Paper may be used for a variety of applications such as recording any pre-existing conditions and recording proof of immunization. It is almost a double standard since the imaging portion of medicine (radiology) went through a film revolution whereby removing the film dependency and going fully digital. Requirements from government and standardization bodies further put the burden on the caregivers to produce more paper so as to validate their compliance.

The caregivers have identified paper generation as a great hindrance in their delivery of effective medicine. While efforts such as digitized record keeping and computer-based office organization systems is abound, paper documents are still used, especially as it pertains to patient interface. Example embodiments of this invention intends to break this barrier by using workflow and methodologies that not only provide sufficient functionality to the caregiver but also can readily be accepted by the patient and be supported in a mobile environment.

Around fifty percent of individuals have access to a personal computer on a regular basis while around ninety percent of patients currently use a cell phone. The use of a portable device as the primary interface to the health care system is advantageous in many aspects. The technical aspects of using a portable device for an intelligent health record management system revolve predominantly around security and authentication. The embodiments of this invention enhance biometric authentication mechanisms for this purpose. First, a certain individual needs to be authenticated so as to either access or provide the permission to access a private health record. Second is the replacement of the health provider's clipboard where patient demographics and health history is usually recorded. Both of these aspects are presented as a mobile feature to further reduce response time and in turn increase efficiency, which is the primary derivative of the embodiments of this invention.

BRIEF SUMMARY

It is an object of the present invention to provide a method and system for a portable Electronic Health Record (EHR) enabled device to perform biometric authentication of a user. The portable EHR enabled device may comprise a memory, a wireless receiver and transmitter, an encryption and decryption module, and an authentication module. The wireless receiver module receives an encrypted message from an EHR database server storing a user health record. The decryption module decrypts the encrypted message using the first decryption key. The decrypted message includes a request to perform a biometric authentication to approve a transaction.

The authentication module may prompt the user to speak a pass phrase and store the spoken voice of the user. The authentication module may create a set of variables. The set of variables are obtained by analyzing the stored spoken voice and may include the pass phrase and at least one more variable characterizing the spoken voice. The authentication module then encrypts a second message using a second encryption key. The second message includes a portable EHR enabled device ID number (or session identification information) and the set of variables. The device transmits the second encrypted message to the EHR database server, wherein the EHR database server analyzes the set of variables to determine the identity of the user. The portable EHR device may receive an encrypted message from the EHR database server determining whether the biometric authentication is successful and the transaction is approved. The determination may be made by the EHR database server and may be based on verifying the portable EHR enabled device ID number (or session identification information), the pass phrase, and the user identity.

It is additionally an object of the present invention to provide a system and method for automatic information transaction between an office system and an EHR database server during an office visit by a user. In an example embodiment, an EHR enabled device may communicate to an office system. The EHR enabled device may transmit a request to the EHR database server. The EHR enabled device may receive an encrypted message from the EHR database server to perform biometric authentication. The EHR enabled device performs biometric authentication of the user. When biometric authentication is successful, the EHR enabled device may provide the user personal information to the office system. The office system may verify if the user health record is on file. If the user health record is on file, then the office system may sign in the user. If the user health record is not on file the office system may receive the user health record from an EHR database server. The office system may send a request to the EHR database server to perform a transaction. Example transactions include validating insurance information, verifying the status of the insurance coverage, or filing intended or anticipated procedures with insurance company for any pre-approval.

It is a further object of the present invention to provide a system and method for enabling a user to access an EHR database server. In another example embodiment, an EHR enabled device may receive a request from a user to access an EHR database server. The EHR enabled device may transmit a request to the EHR database server. The EHR enabled device may receive an encrypted message from the EHR database server to perform biometric authentication. The EHR enabled device may perform biometric authentication and when the biometric authentication is successful, the user may request for direct delivery of the health record to the EHR enabled device. The user may also request for delivery of the health record for an impending request by an office system. Access to the EHR database server may be available for use by the office system for a limited time period.

It is a still further object of the present invention to provide a system and method for notifying a user about a transaction request from an EHR database server. In another example embodiment, an office system may request access to a user health record from an EHR database server without an existing authentication session for the user. The office system may be notified of the anticipated delay. The user may receive a message from the EHR database server that the office system is requesting access to the user health record. The EHR enabled device may perform biometric authentication. When the biometric authentication is successful, the EHR database server may notify the office system that the user health record is available. The EHR database server may transfer the user health record to the office system.

It is a still further object of the present invention to provide a system and method for an EHR Database Server. The EHR database server 203 performs biometric authentication of a user 205. The EHR database server 203 may store a first encryption key in a memory. The EHR database server may encrypt a first message using the first encryption key. The encryption is performed by an encryption module. The first encrypted message may include a request to perform a biometric authentication to approve a transaction. The EHR database server 203 transmits the first encrypted message to a portable EHR enabled device 202, wherein the portable EHR enabled device may prompt the user 205 to speak a pass phrase. The first The EHR database server 203 receives a second encrypted message from the portable EHR enabled device 202 via the transceiver module. The EHR database server 203 may decrypt the second message using a second decryption key. The second message may include a portable EHR enabled device ID number (or session identification information)and a plurality of variables. The plurality of variables may include the pass phrase and at least one more variable characterizing the spoken voice of the user. The authentication module in the EHR database server 203 may analyze the plurality of variables to determine the identity of the user. The EHR database server may transmit a third encrypted message to the portable EHR enabled device determining whether the biometric authentication is successful and the transaction is approved. The determination may be based on verifying the portable EHR enabled device ID number (or session identification information), the pass phrase, and the user identity.

These and other objects and features of the present invention will become more apparent from the following detailed description of the present invention considered in connection with the accompanying drawings which disclose an embodiment of the present invention. It should be understood, however, that drawings, as well as the description, are presented here for the purpose of illustration only and not as a definition of the limits of the invention.

DETAILED DESCRIPTION OF EMBODIMENTS

Embodiments of the present invention performs biometric authentication to approve a transaction.

Example embodiments of the present invention proposes a secure intelligent health record management system, which ensures patient privacy with biometric authentication and near real time mobile access, can lower the cost, and improve the quality and access for medical care. An important benefit of this system is automated transfer of basic patient information. Biometrics authentication is done via mobile access, by verifying that the cell phone can only be accessed by its rightful owner and by uniqueness of the patient's voiceprint. Mobile access is provided by modification of existing protocols in records management systems. The proposed system brings mobility to patient access and authorization while protecting privacy.

The embodiments of this invention deal with a fully online system with real time access. In this environment all the stakeholders may interoperate and share information regarding the procedures and processes. Implementation of an intelligent health record management system is an important step in this process. One of the major sources of malpractice claims are poor handwriting, and poor record management as to who performed what procedure on which patient and for what reason. An intelligent health record management system disclosed in the embodiments of this invention may help reduce medical errors and a better legal defense for the providers of medical care.

A huge cost reduction would be realized if there is a single standardized electronic health record to be kept and maintained. This cost saving has direct effect on the patient's cost of receiving health care. The health care provider, claim adjuster, and insurance company all have access to real time data, which can facilitate a speedy payment system.

Introduction of technology has always created social challenge in healthcare systems. The embodiments of this invention implement technology to deliver efficiency to the healthcare system. Using cell phone as the basic building block of health care authorization of access would have been a major social upheaval a decade ago. Today cell phone is one of the primary means of communication. The embodiments of this invention bring the mobility of access to stakeholders in the health care system. The patient may use the mobility to authorize access to his or her own record. This near real-time authorization has ripple effect in efficiency of access for healthcare providers, and health insurance organizations. This is one of the aspects of this invention. So far near real-time access was possible, but the issue of protection of privacy was not resolved. The embodiments of this invention resolve the problem of protection of privacy via secure biometric authentication. This may be done by developing a privacy enhancing technology and allowing real-time access to data that may accelerate the adoption of this privacy enhancing technology.

Figure 1:
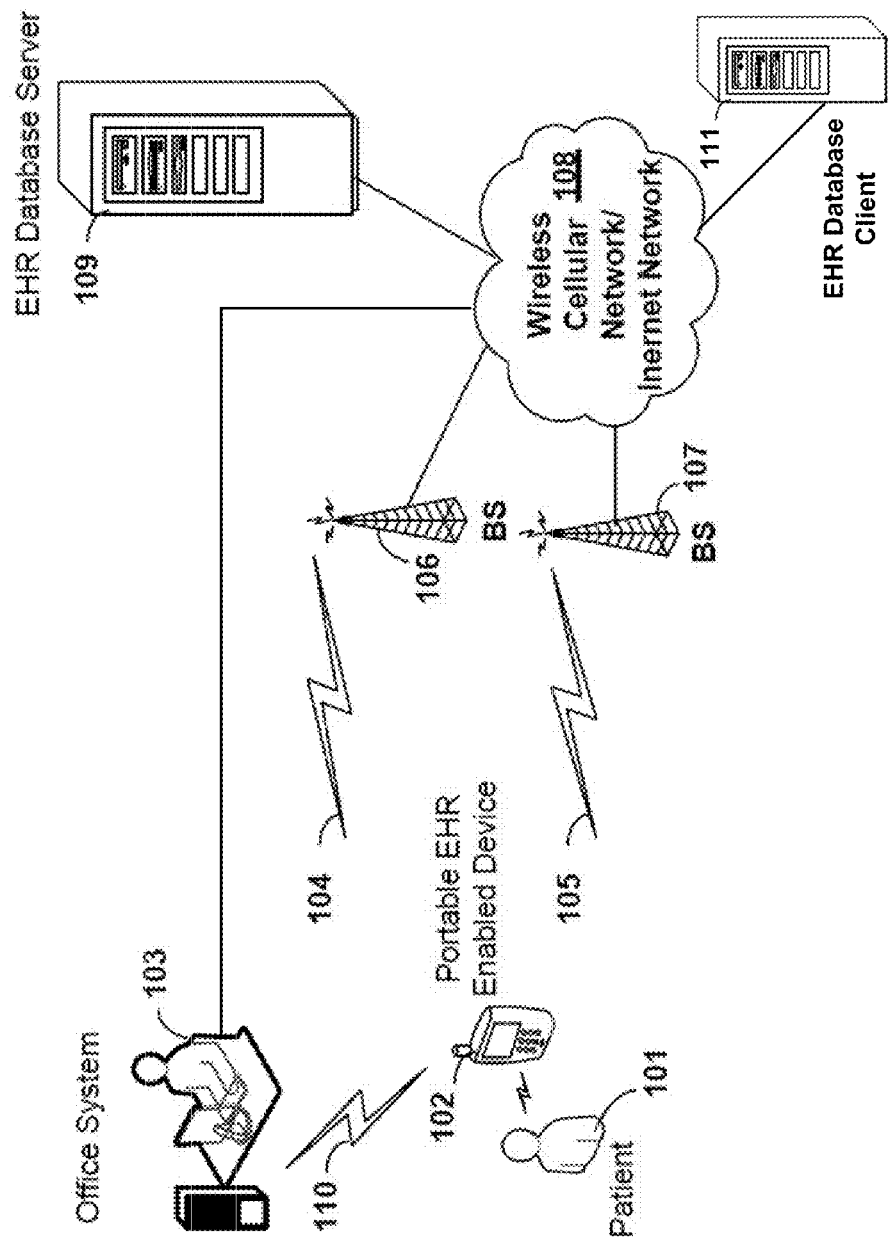
FIG. 1 is a simplified block diagram depicting an intelligent health record management system in which an exemplary embodiment of the invention can be implemented.

FIG. 1 is a simplified block diagram depicting an intelligent health record management system in which an exemplary embodiment of the invention can be implemented. As shown, the system includes at its core a Wireless Cellular Network/Internet Network 108, which may function to provide connectivity between one or more access terminals (portable EHR Enable Device) 102 (e.g., a cell phone, PDA, or other wirelessly-equipped device), and one or more database servers, such as an EHR Database Server 109 and EHR Database Client 111, and an Office System 103.

It should be understood, however, that this and other arrangements described herein are set forth for purposes of example only. As such, those skilled in the art will appreciate that other arrangements and other elements (e.g., machines, interfaces, functions, orders of functions, etc.) can be used instead, some elements may be added, and some elements may be omitted altogether. Further, as in most telecommunications applications, those skilled in the art will appreciate that many of the elements described herein are functional entities that may be implemented as discrete or distributed components or in conjunction with other components, and in any suitable combination and location. Still further, various functions described herein as being performed by one or more entities may be carried out by hardware, firmware and/or software logic. For instance, various functions may be carried out by a processor executing a set of machine language instructions stored in memory.

As shown, the access network may include a plurality of base stations 106-107. Each base station 106-107 of the access network may function to transmit and receive RF radiation 104-105 at one or more carrier frequencies, and the RF radiation may then provide one or more air interfaces over which the access terminal 102 may communicate with the base stations 106-107. The user 101 uses the wireless device to perform biometric authentication. The user for example may be a patient in a doctor's office.

Each of the one or more base stations 106-107 may define a corresponding wireless coverage area. The RF radiation 104-105 of the base stations 106-107 may carry communications between the Wireless Cellular Network/Internet Network 108 and access terminal 102 according to any of a variety of protocols. For example, RF radiation 104-105 may carry communications according to CDMA (e.g., 1xRTT, EVDO), iDEN, TDMA, AMPS, GSM, GPRS, UMTS, EDGE, WiMAX (e.g., IEEE 802.16), LTE, microwave, satellite, MMDS, Wi-Fi (e.g., IEEE 802.11), Bluetooth, infrared, and other protocols now known or later developed.

As shown, the office system 103 may be connected to Wireless Cellular Network/Internet Network 108 through a wireline or wireless technology. The portable EHR Enable Device 102 may be able to communicate with the office system 103 via a short range wireless technology 110, for example Bluetooth, infrared or Wi-Fi, or a cellular wireless technology, or a wireline technology such as USB, Ethernet or any other physical medium. The communication among Office System 103, Portable EHR Enabled Device 102, EHR Database Server 109, and EHR Database Client 111 may be enabled by any networking and transport technology for example TCP/IP or any other networking protocol.

Figure 2:
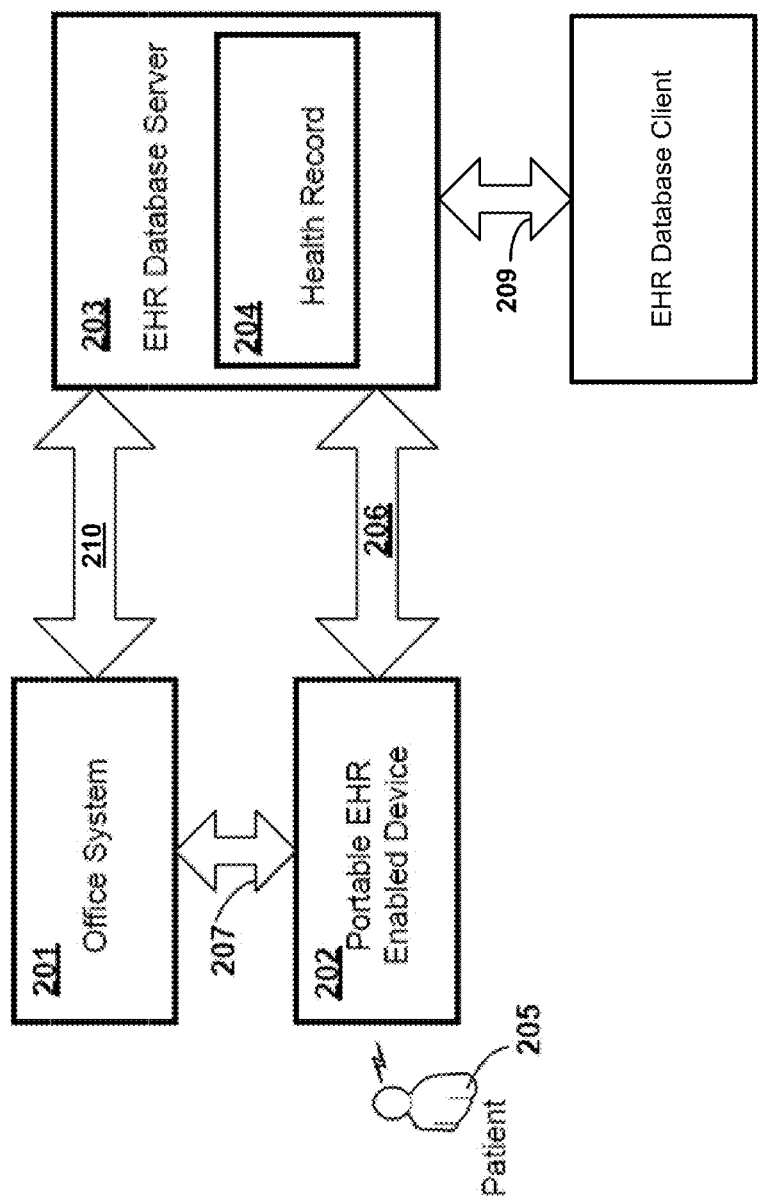
FIG. 2 is a simplified block diagram depicting the interconnections in an intelligent health record management system in which an exemplary embodiment of the invention can be implemented.

FIG. 2 is a simplified block diagram depicting the interconnections in an intelligent health record management system in which an exemplary embodiment of the invention can be implemented. The office system 201 may be a provider's office, an insurance company or a government entity. The office system 201 communicates with the portable EHR enabled device 202 via interface 207. The portable EHR enabled device 202 may be a cell phone, a smart phone, or a portable personal computer. The portable EHR enabled device 202 is able to process the voice of the user 205. The user 205 in an example embodiment is a patient. The office System 201 communicates with the EHR Database Server 203 via interface 210. The EHR Database Server 203 may include a patient's health records. The health record data may include user's information such as the user demographics, user medical insurance, an employment status, a responsible individual, pre-existing conditions or the user's medical history. EHR Database Server 203 may communicate with a portable EHR enabled device 202 via interface 206. EHR Database Server 203 may also communicate with a EHR Database Client 208 via interface 209.

The voice recognition biometric application may be developed for use on a cell phone device. This cell phone device may have an open architecture where the application can be used on a variety of manufacturer's devices. Interface programs may be developed between the EHR software system and the cell phone biometric application for both data input and patient notification applications.

This invention leap frogs existing technology in ensuring patient's health record protection by providing a biometric component to the patient record ensuring that records being updated are for the correct patient. In lieu of a health card, an open application residing on the patient's cell phone verifies the voice of the patient in addition to any password protection that may also be used. Additionally, access to the patient health record may be tracked and for actions requiring the patient's approval a secure text message may be sent to the patient's phone for their knowledge and approval. The voice biometric authentication mechanism may be required for patient approval. Breaches of privacy of the patient record are reduced and notifications of data base issues can be sent immediately to the patient for action.

The use of a biometric technology with a cell phone offers safeguards that may not be possible without a high cost for readers and a much higher level of sophistication at the provider site. The actual health record may or may not reside on the cell phone. A subset of insurance or general information may be tied to the individual's phone but in any case this information may be accessible with the appropriate biometric and password if needed.

Figure 3:
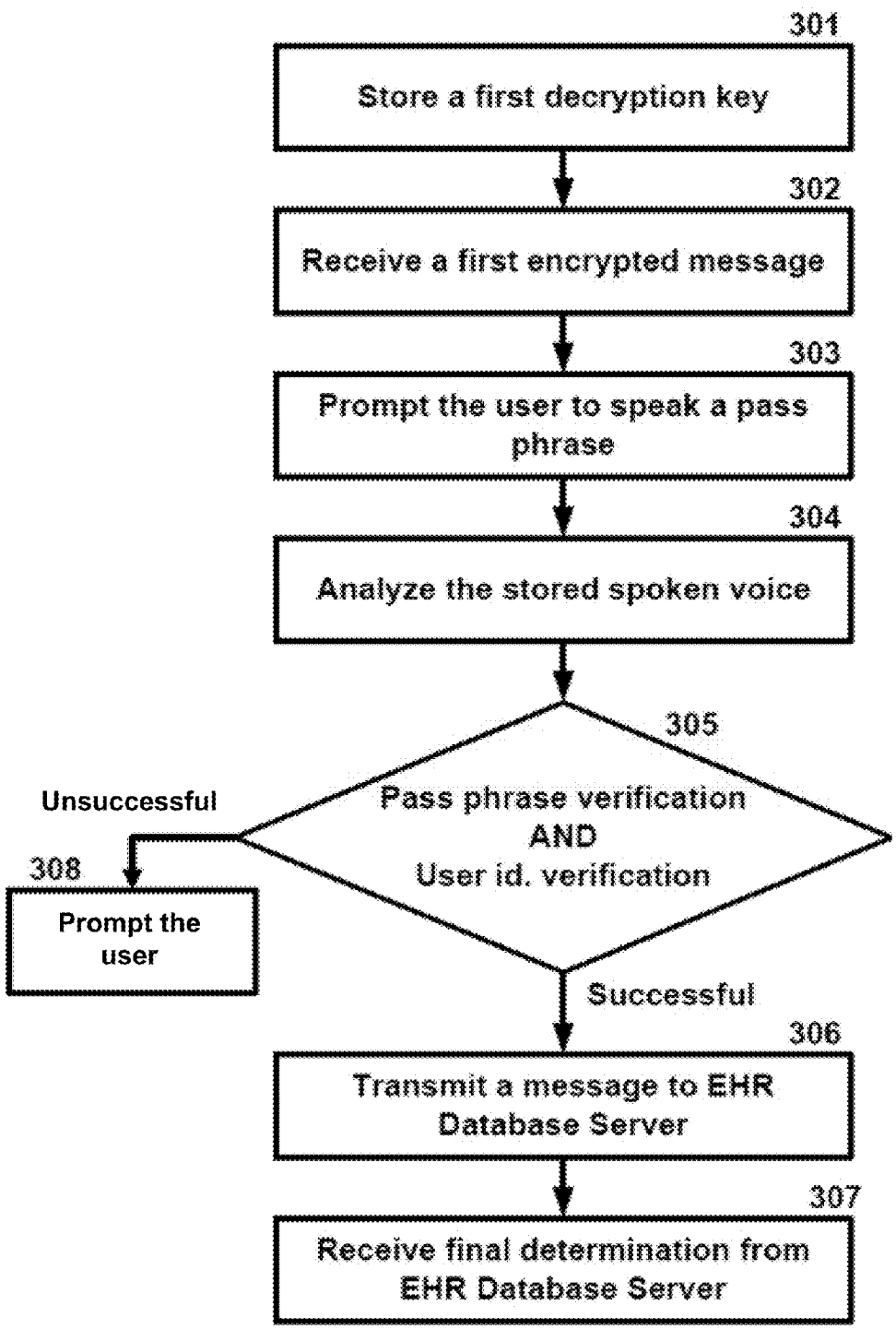
FIG. 3 is a first example flow chart for biometric authentication according to one aspect of the illustrative embodiments.

FIG. 3 is a first example flow chart for biometric authentication according to one aspect of the illustrative embodiments. The flow chart shows a method for a portable EHR enabled device 202 to perform biometric authentication of a user 205. The portable EHR enabled device 202 may store a first decryption key in process 301. The portable EHR enabled device 202 may receive a first encrypted message from an EHR database server 203 in process 302. The first message may be received via a wireless interface. The EHR database server 203 may store the user health record 204.

The portable EHR enabled device 202 decrypts the first encrypted message using the first decryption key. The first decrypted message may include a request to perform a biometric authentication to approve a transaction. In process 303, the portable EHR enabled device 202 may prompt the user 205 to speak a pass phrase and store the spoken voice of the user. In process 304, the portable EHR enabled device 202 may analyze the stored spoken voice.

The portable EHR enabled device 202 may verify the pass phrase spoken by the user by analyzing the stored spoken voice. It may also verify the identity of the user by analyzing characteristics of the stored spoken voice. In verification 305, the portable EHR enabled device 202 verifies if the pass phrase verification is successful and the user identification verification is successful. If both verifications are successful, it then encrypts a second message using a second encryption key, the second message includes a portable EHR enabled device ID number(or session identification information), the pass phrase, and the user identity. The portable EHR enabled device 202 may wirelessly transmit the second encrypted message to the EHR database server 203, in process 306. In process 307, the portable EHR enabled device 202 may receive a third encrypted message from the EHR database server determining whether the biometric authentication is successful and the transaction is approved. If the verification 305 is unsuccessful, the portable EHR enabled device 202 may prompt the user in process 308 to take further actions or may inform the user about the authentication outcome.

Figure 4:
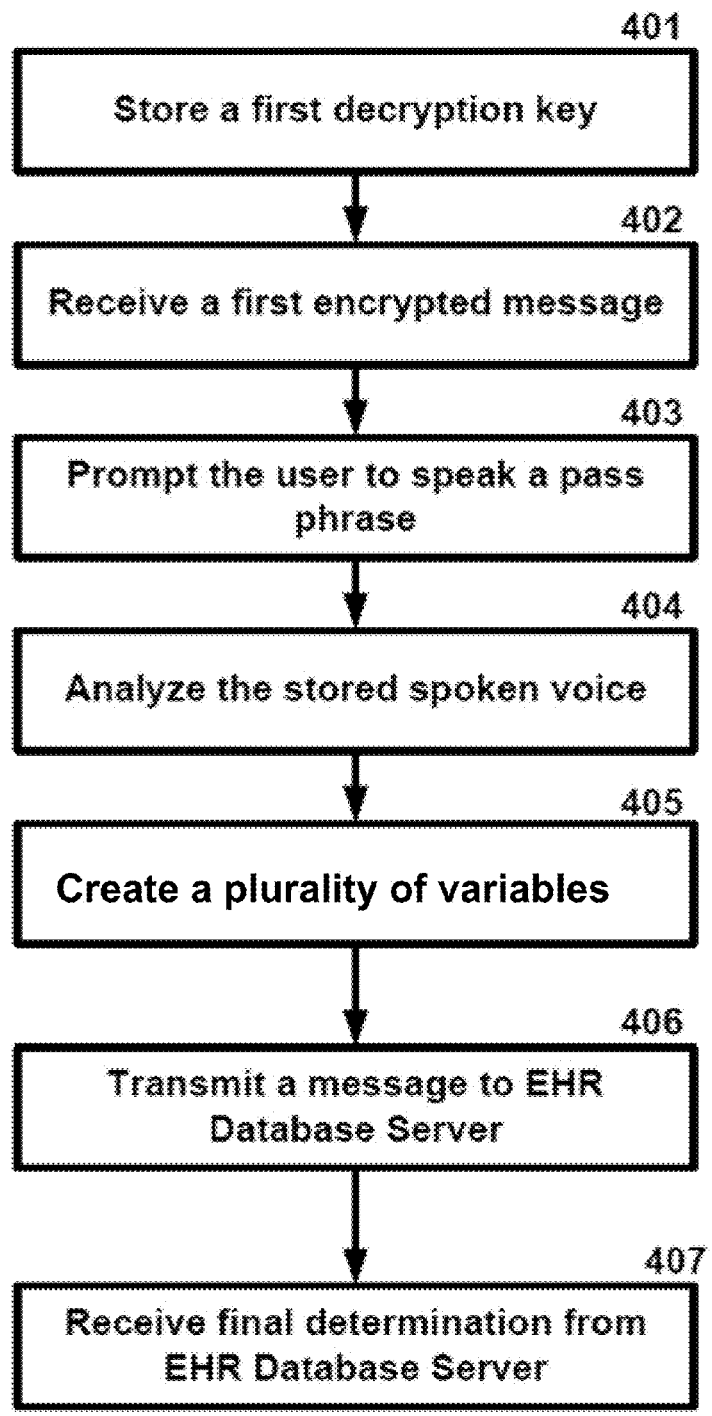
FIG. 4 is a second example flow chart for biometric authentication according to one aspect of the illustrative embodiments.

FIG. 4 is a second example flow chart for biometric authentication according to one aspect of the illustrative embodiments. The flow chart shows a method for a portable EHR enabled device 202 to perform biometric authentication of a user 205. The portable EHR enabled device 202 may store a first decryption key in process 401. The portable EHR enabled device 202 may receive a first encrypted message from an EHR database server 203 in process 402. The first message may be received via a wireless interface. The EHR database server 203 may store the user health record 204.

The portable EHR enabled device 202 decrypts the first encrypted message using the first decryption key. The first decrypted message may include a request to perform a biometric authentication to approve a transaction. In process 403, the portable EHR enabled device 202 may prompt the user 205 to speak a pass phrase and store the spoken voice of the user. In process 404, the portable EHR enabled device 202 may analyze the stored spoken voice. It also may create a plurality of variables including the pass phrase and at least one more variable characterizing the spoken voice, in process 405.

The EHR enabled device 202 may generate an encrypted second message using a second encryption key. The second message may include a portable EHR enabled device ID number (or session identification information)and the plurality of variables. In process 406, the EHR enabled device 202 transmits the second encrypted message to the EHR database server 203. The EHR database server 203 may analyze the plurality of variables to determine the identity of the user. The EHR enabled device 202 receives a third encrypted message including the final determination from the EHR database server 203 in process 407. The third encrypted message determines whether the biometric authentication is successful and the transaction is approved. The determination may be made by the EHR database server 203 and is based on verifying the portable EHR enabled device ID number(or session identification information), the pass phrase, and the user identity.

Verifying of the identity of the user 205 may comprise analysis of the uniqueness of the user voiceprint.

The EHR database server 203 determines a successful biometric authentication if the portable EHR enabled device ID number(or session identification information), pass phrase, and speaker identity matches with the user health record data. The portable EHR enabled device ID number(or session identification information)may be one of the following: the portable EHR enabled device phone number, the portable EHR enabled device IP address, the portable EHR enabled device MAC address, the portable EHR enabled device IMSI number, and the portable EHR enabled device IMEI number.

EHR database server 203 provides a substantially real-time response determining whether the biometric authentication is successful. EHR database server 203 may log access to the EHR database server for tracking purposes. The EHR database server 203 may send notifications of database issues to the user 205. The EHR database server 203 may tie the user health record data to the portable EHR enabled device ID number (or session identification information)of the user 205.

Figure 5:
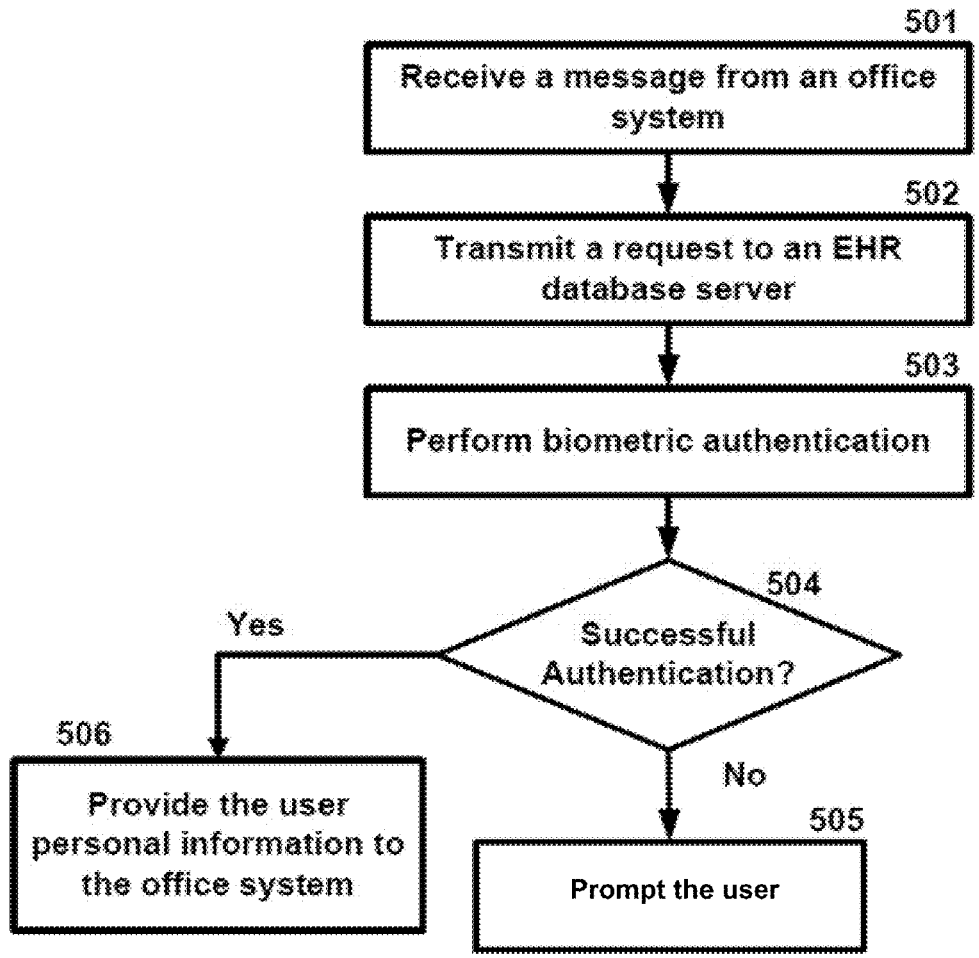
FIG. 5 is a first example flow chart for enabling an office system to communicate data with an EHR database server according to one aspect of the illustrative embodiments.

It is additionally an object of the present invention to provide a system and method for automatic information transaction between an office system 207 and an EHR database server 203 during an office visit by a user 205. FIG. 5 is a first example flow chart for enabling an office system to communicate data with an EHR database server according to one aspect of the illustrative embodiments. In this example embodiment, an EHR enabled device 202 may communicate to an office system and receive a message as shown in process 501. The EHR enabled device 202 may transmit a request to the EHR database server 203, in process 502. The EHR enabled device 202 may receive an encrypted message from the EHR database server 203 to perform biometric authentication. The EHR enabled device 202 performs biometric authentication of the user in process 503 according to one of the biometric authentication methods disclosed in this specification. In verification 504, if biometric authentication is successful, the EHR enabled device may provide the user personal information to the office system 201 in process 506. If biometric authentication is unsuccessful, the EHR enabled device may prompt the user requesting further actions or just informing the user about the authentication outcome as shown in process 505.

Figure 6:
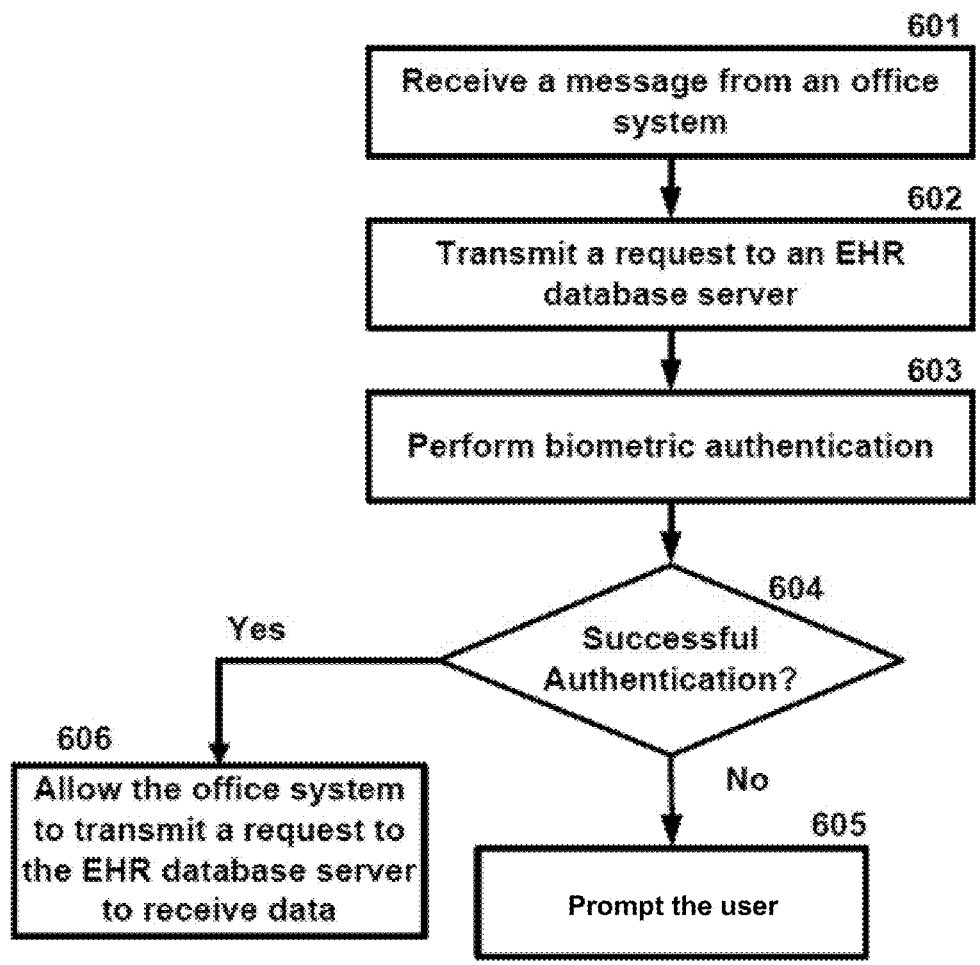
FIG. 6 is a second example flow chart for enabling an office system to communicate data with an EHR database server according to one aspect of the illustrative embodiments.

FIG. 6 is a second example flow chart for enabling an office system to communicate data with an EHR database server according to one aspect of the illustrative embodiments. In this example embodiment, an EHR enabled device 202 may communicate to an office system and receive a message as shown in process 601. The EHR enabled device 202 may transmit a request to the EHR database server 203, in process 602. The EHR enabled device 202 may receive an encrypted message from the EHR database server 203 to perform biometric authentication. The EHR enabled device 202 performs biometric authentication of the user in process 603 according to one of the biometric authentication methods disclosed in this specification. In verification 604, when biometric authentication is successful, it allows the office system to transmit a request to the EHR database server to receive data in process 606. The office system may verify if the user health record is on file. If the user health record is on file, then the office system 201 may sign in the user. If the user health record is not on file the office system may receive the user health record 204 from an EHR database server 203. The office system 201 may send a request to the EHR database server 203 to perform a transaction. Example transactions include validating insurance information, verifying the status of the insurance coverage, or filing intended or anticipated procedures with insurance company for any pre-approval. If biometric authentication is unsuccessful, the EHR enabled device may prompt the user requesting further actions or just informing the user about the authentication outcome as shown in process 605.

Figure 7:
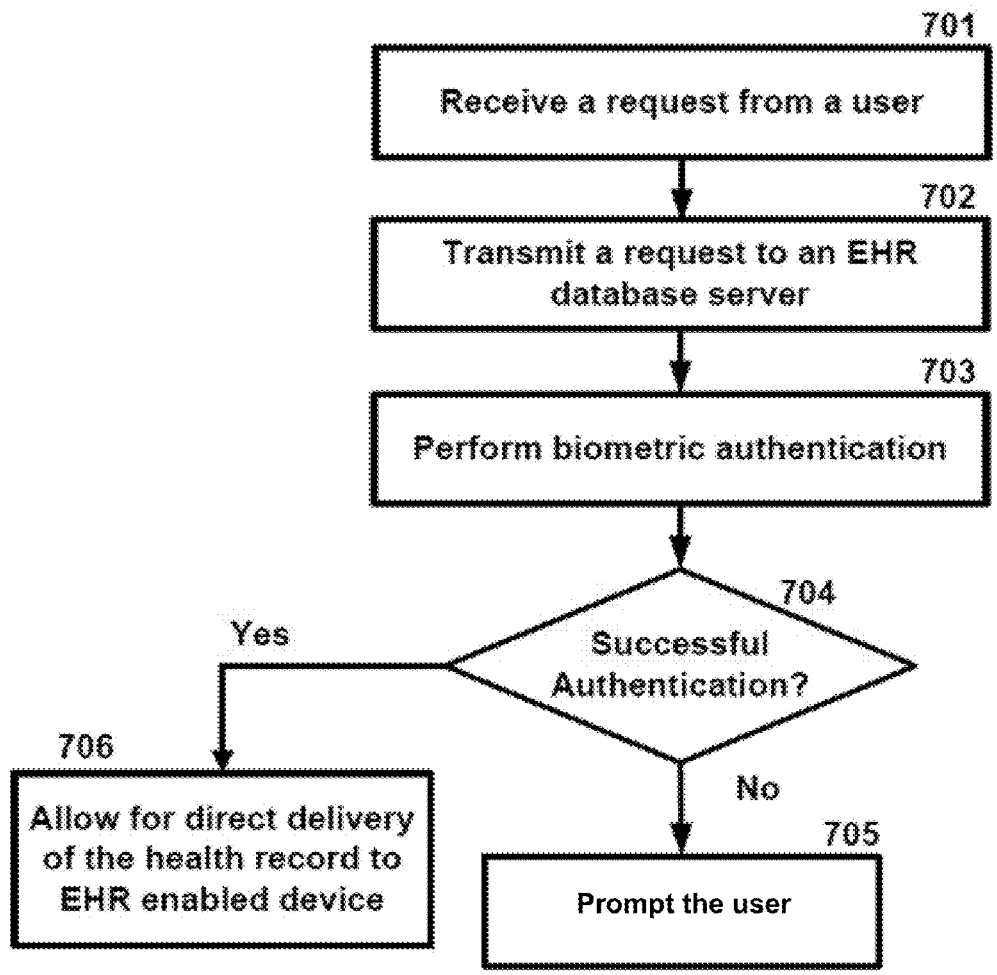
FIG. 7 is an example flow chart for enabling a user to access an EHR database server according to one aspect of the illustrative embodiments.

It is a further object of the present invention to provide a system and method for enabling a user 205 to access an EHR database server 203. FIG. 7 is an example flow chart for enabling a user to access an EHR database server according to one aspect of the illustrative embodiments. An EHR enabled device 202 may receive a request from a user to access an EHR database server in process 701. The EHR enabled device 202 may transmit a request to the EHR database server 203 in process 702. The EHR enabled device may receive an encrypted message from the EHR database server to perform biometric authentication in process 703. The EHR enabled device may perform biometric authentication and verify the outcome in verification process 704. If the biometric authentication is successful, the user may request for direct delivery of the health record to the EHR enabled device 202 in process 706. The user may also request for delivery of the health record for an impending request by an office system. Access to the EHR database server may be available for use by the office system for a limited time period. If biometric authentication is unsuccessful, the EHR enabled device may prompt the user requesting further actions or just informing the user about the authentication outcome as shown in process 705.

It is a still further object of the present invention to provide a system and method for notifying a user 205 about a transaction request from an EHR database server 203. In another example embodiment, an office system 201 may request access to a user health record 204 from an EHR database server without an existing authentication session for the user. The office system 201 may be notified of the anticipated delay. The user 205 may receive a message from the EHR database server that the office system is requesting access to the user health record. The EHR enabled device 202 may perform biometric authentication. When the biometric authentication is successful, the EHR database server may notify the office system that the user health record is available. The EHR database server may transfer the user health record to the office system.

It is a still further object of the present invention to provide a portable EHR enabled device 201. The portable EHR enabled device may comprise a memory, a wireless receiver and transmitter, an encryption and decryption module, and an authentication module. The memory may be configured to store a decryption key. The wireless receiver module receives an encrypted message from an EHR database server storing a user health record. The decryption module decrypts the encrypted message using the first decryption key. The decrypted message includes a request to perform a biometric authentication to approve a transaction.

In another example embodiment of the invention a system and method for an EHR Database Server is disclosed. The EHR database server 203 performs biometric authentication of a user 205. The EHR database server 203 may store a first encryption key in a memory. The EHR database server may encrypt a first message using the first encryption key. The encryption is performed by an encryption module. The first encrypted message may include a request to perform a biometric authentication to approve a transaction. The EHR database server 203 transmits the first encrypted message to a portable EHR enabled device 202, wherein the portable EHR enabled device may prompt the user 205 to speak a pass phrase. The first encrypted message is transmitted using a transceiver module.

The EHR database server 203 receives a second encrypted message from the portable EHR enabled device 202 via the transceiver module. The EHR database server 203 may decrypt the second message using a second decryption key. The second message may include a portable EHR enabled device ID number(or session identification information)and a plurality of variables. The plurality of variables may include the pass phrase and at least one more variable characterizing the spoken voice of the user. The authentication module in the EHR database server 203 may analyze the plurality of variables to determine the identity of the user. The EHR database server may transmit a third encrypted message to the portable EHR enabled device determining whether the biometric authentication is successful and the transaction is approved. The determination may be based on verifying the portable EHR enabled device ID number(or session identification information), the pass phrase, and the user identity.

The authentication module may prompt the user to speak a pass phrase and store the spoken voice of the user. The authentication module may create a set of variables. The set of variables are obtained by analyzing the stored spoken voice and may include the pass phrase and at least one more variable characterizing the spoken voice. The authentication module then encrypts a second message using a second encryption key. The second message includes a portable EHR enabled device ID number (or session identification information)and the set of variables. The device transmits the second encrypted message to the EHR database server, wherein the EHR database server analyzes the set of variables to determine the identity of the user. The portable EHR device may receive an encrypted message from the EHR database server determining whether the biometric authentication is successful and the transaction is approved. The determination may be made by the EHR database server and may be based on verifying the portable EHR enabled device ID number(or session identification information), the pass phrase, and the user identity.

The centerpiece of this system is the patient. Given any scenario, privacy is dictated by the use of biometric authentication. This may tie the patient to an agile and mobile permission slip that only the patient, provider, and information system may use in limited amount. The premise is that an EHR system acts as a safe deposit box whereby a health record may be released when a validated permission slip is presented to it. Issues of security are addressed here to guarantee this process. The Permission slip may be authenticated by the user, which in turn ensures that the patient is the ultimate gatekeeper to his or her own data. The permission slip may need to travel with the data to ensure that the data is kept confidential. The use terms of the permission slip is then conveyed as the data resides within the provider and third party systems. In the disclosed embodiments, the access to the EHR database server 203 may be available for use by the office system 201, the EHR Database Client 208, or the user 205 for a limited time period.

Biometric-based User Authentication

The Biometric portion of the embodiments of this invention is geared toward use of voice recognition and verification. There are various workflow paths available in implementing a suitable voice recognition system including enrollment of a user, text dependent or independent, local recognition or server based recognition among others. Example embodiments of this invention may use a specific key tailored to each user such as their name to achieve high probabilities of correct identification while keeping the probabilities of false alarms manageable. There are also ranges of algorithms available such as frequency estimation, hidden Markov models, Pattern matching, neural networks, decision trees, Gaussian mixture models and matrix representations among others. The unique factors affecting our implementation are processing power, local memory and latency, which affect both a mobile and a server implementation.

Such systems have been commercialized in various industries such as Defense, cockpit voice command interface, Medical, voice transcripts, Word Processing, such as Dragon speaking where a user can speak a document, and an assortments of telephony applications geared towards customer service. None of these systems operate on the same set of requirements that are set in the embodiments of this invention.

Markov Models may aim at solving the problem of speaker recognition. Markov Models whereby hidden states may be linked and revealed based on a large variety of parameters. These class of methods may articulate time series dependencies that formulates the way we talk in a way that we perceive as accent, voice pitch, language, choice of words and an array of parameters that may not be easily described. A system may combine acoustic, phonotactic and Prosodic subsystems for purposes of standardizing algorithm performance. Spectral information may provide information about the speaker's vocal tract which literally opens a whole world of estimation and detection algorithms to provide input in this area. Extension of this is a class of phonetic parametric estimators whereby time series dependencies on spectral signatures may provide how a speaker provides spectral range while speaking. Higher level understanding such as natural language, choice of words and grammar also provides an axis in detailing speaker recognition.

In the embodiments disclosed in this specification, the process behind speaker recognition algorithm may be the process of parameter estimation and recognition through a proper feature extraction methodology that may enable detection. Given an input audio signal, the most general premise is to first perform feature extraction. Feature extraction may be as simple as modifying the time series sample by adding gain for example to as complicated as extracting phonetics to estimate a spoken word. The extracted features carry within them characteristics whereby they try to estimate some sort of underlying phenomenology. These features may then be processed by a pattern analysis system whereby the system can either recognize a parameter or estimate it. The process of recognition or estimation is one process whereby recognition may have a binary output but estimation may have more complex output such as real numbers. The estimated or recognized parameters may then go through a detection algorithm which at times may be called a classifier to identify the speaker.

An example of spectral analysis for speaker recognition, such as the general shift in frequency between males and females, simply processes the audio signal by taking the frequency transform. A Fast Fourier Transform of the audio signal provides a rich set of features that may be generated. The frequency coefficients may then be processed by the pattern analysis component to provide an estimate of something such as pitch. The average frequency present in the set of coefficients may provide an estimate of such a measure. But the estimate may not be an identification of a male or female. A threshold on the average value may provide this detection.

The three different processes identified above may provide a basis for any voice recognition to operate on a mobile environment where the aim is to identify a single user. Each and every process may have a more complicated set of processes as identified above. For example, a wavelet transform may provide a different set of features than a Fast Fourier Transform and in actuality there exists a large array of transforms that may provide a rich feature set for any algorithm. Estimation or recognition may also range with measures such as standard deviation, high order means, likelihood ratios, statistically motivated and so on. Similarly detection algorithms such as Neural Network, optimization methodologies, Principle Component Analysis and a recently common method of Support Vector Machines may be used to augment this process.

On-Demand Patient Information

Once caregivers identify that they need access to the patient's records they simply initiate a task on their information management system which in turn sends a message to the user by text message, email, or other low latency medium with a set of embedded information and instructions. Upon successful voice recognition, the system would unlock the patient's record and make it available to the caregiver. The amount of time needed for the complete transmission may literally be orders of magnitude less than current methodologies.

The replacement of the clipboard may provide enormous cost savings but with a much simpler workflow. The embodiments of this invention may utilize current wireless access technologies that are already available in smart phones today. The best access media is Bluetooth (BT) access where a Radio Frequency (RF) signal makes a digital connection between two computing nodes.

Some of the common profiles are headset profile, which are used in mobile phones, synchronization profile, which is used in smart phones for contacts and personal information synchronization, and wireless data network access, which is available in some smart phones to provide Internet access to a host computer. Just about any profile can be used for these purposes since digital data is passed via this medium. The embodiments of this invention may use any communication profile that may be available in the future so as to guarantee the enablement to use such a technology for this purpose.

The needed information may be stored in the mobile phone via a mobile phone application, web-based interface or a workstation interface. This may include patient demographics, insurance, employment, responsible individual, pre-existing conditions and medical history. Then upon entry to the doctor's office for the first time, the phone may be used to transfer the data after connecting with the on-site system. Future visits to the same office may benefit from not having to sign in but rather perform an electronic sign-in.

In an example scenario, when the patient has a pre-existing condition and the patient delete it from the records somehow. The doctor sees the patient and mentions that as I see here the patient has no pre-existing condition and the patient agrees even if the doctor lists the conditions that are important. Still the patient may say that there is no pre-existing condition. The doctor then may send a request to the EHR system that requests the patient to authenticate. This will go in the record just like a signature as if the doctor provided a sheet or asked information and required the patient to sign. In case the doctor then prescribes to a certain treatment that may not be correct for the existing condition that he is now legally covered. Specially based on hospital and in office treatments there exists a lot of paperwork that the user has to first agree to before any procedure takes place. In these cases the patient approval is performed by the authentication method described in this invention.

Providing secure access in both of these scenarios is needed. There are several ways of achieving a secure communication medium which would differ by workflow and time-line processes. The embodiments of this invention provide a sufficiently simple workflow while not sacrificing security. For example, the request to access health records may be time limited and as such the key generated by the system may have a time limit feature. Upon successful deciphering of the incoming message in the patient's phone, the authentication application generates a secure return code, which embeds the voice recognition features within. The actual code may not know if the correct speaker is being identified or not. Once the return code is received by the information management system, it may authenticate its validity and further validate the voice recognition parameters to match those of the speaker's. If an incorrect reception is identified another message may be sent to the user. The number of messages sent to the user may be limited and once that limit is reached the paper option may be triggered. Similarly, transfer of patient information via Bluetooth may be done via a secure medium.

The security method may include a large numbers of dependencies and the ability to keep the items secret. That means adding as many keys as possible, dependent on things that are secret and only decipherable in a controlled environment. The security method may perform this in as many places as possible.

When an EHR database server 203 sends a request to authenticate a user, the request may be encrypted with keys that would depend on a lot of variables such as time of day, the recipient phone number, social security number, home address and others. The message may also include a return encryption key that would be used to generate an encrypted return message with the biometric authentication included. The reason for including time of day, recipient phone number and other identifying features is that this would be the information available to the EHR system and that the system is operating in a cold call format. That is to say that the system initiates a request and there may be no other dependencies to exploit. The reason for providing additional keys for the return message is to make it harder for a node to send messages to the server without an associated request.

Once the message is received by the mobile device 202, decrypted and interfaced with the user to show the information regarding the record transfer the process of authentication resumes. In the embodiments of this invention, a voice authentication is used that yields a graceful degradation along with provision for proper transmission. This may be done by extracting voice identification features that are extremely redundant in a way that a small amount of feature match would generate a high level of authentication. These features may be extracted from the voice print and spoken phrase in a way that is enabling. The set of features then may get used to not only provide a signature to be compared to the one in the server but also to encrypt the remaining message. The server may decrypt the message once the voice print match is accomplished.

The message that is sent by the mobile device 202 to the server is not obvious in that a simplified message is the permission to transfer the record. However, the message in this case can be the additional keys that the server sent in its original request to the mobile device. The communication from the server to the mobile device in the first transfer may rely on keys that are static and known to both systems. For the return transmission though there is an opportunity to either encrypt based on the voice print, on the keys sent through the forward transmission or simply use the static keys that the forward transmission used. The dependency on which keys are used for the return message and any hierarchical dependencies may be limited to the implementation.

Many example variables characterizing the spoken voice are described here. Any estimation, detection or classification algorithm outputs a variable indicating a particular measure of an arbitrary space. A detection algorithm can be as simple as a single binary output and an estimation can be as complex as a transform domain representation such as a wavelet transform. A simple and well defined algorithm may benefit from a low number of variables and a complex algorithm may utilize a large number of variables. These variables are then eventually used for the purpose of uniquely identifying a person but the size and complexity of the variables may aid in encryption and graceful degradation of a suitable end product. Variables such as audio frequency bands, length of audio, pitch combination, phonetic combination may be used in raw format or in an encrypted or convoluted format. Eventually, the information required to discriminate the intended user with others can be designed into a suitable product with high detection rate, low false alarms and high security, all within one umbrella.

As described in the example embodiments of the invention. The authentication process may use a device ID number or a unique session ID number for authenticating a user. An EHR database server may use a texting service to send a request to a mobile device to request for permission and subsequent authentication. The texting service provides information about the mobile device of at least a phone number and potentially other unique identification numbers which can be readily available from cellular providers. This known and registered path can be included in a workflow of the EHR database server allowing information to be extracted and used to supplement the authentication process. However, if an EHR database server elects to send an email instead, the email can be received in a number of ways. The workflow can be limited to receiving an email only on a mobile device so that an application on the mobile device consumes the email information but this same email can easily be rerouted to other mobile devices. Keeping an information database of registered nodes for allowable return message is difficult but the need to supplement the authentication process is still needed. This may be done by including other unique identifiers in the session such as the content of the original request. Another method that is easily implemented is the registration of the downloaded application on the smart phone to include information that connects the application with the user and can aid in the authentication process. These are all examples of metadata that can be used in the encryption of the return message to the EHR database that does not include any voice-related parameters.

The potential problems of security are two folds. One may intercept a message and decrypt the message. The other is to act as a node such as the server (send and receive) or the mobile device. These methods of keying, encryption and authentication aims to limit the effect of these problems.

System Development

The components of this invention may entail workflow development, technology development, system integration, and development of training modules. Workflow development is an integral part of this invention as much as development of the base science since a true exploitation of science can only occur if it is available in a suitable medium. Due to various issues of new technology availability a suitable training program may be developed and implemented for improved acceptability. This process may take place with an existing system that already has experience and history in providing services to the intended users.

Example embodiments of this invention model the clinical workflow of patient admission and care offered at a care facility. This workflow is translated into application requirements that may be used to generate functional specifications in order to develop the anticipated mobile application for Secure Intelligent Health Record Management System. Major processes and activities in the workflow as well as the relationships governing these processes and activities may be modeled for implementation of this invention. This study may be divided into the following three phases:

Phase 1: In this phase, preliminary observations may used to identify situations, events, and time periods during the patient care that are of critical importance, called critical points (CPs). The importance of these points is reflected by the level of impact on the overall workflow caused by the disruption or interruption of the activities related to these points.

Phase 2: In this phase, direct observations and structured interviews may be used to identify and define the activities related to each CP in the patient care. For each activity, interaction between participants, processes, technology and information flow may be thoroughly documented. Special attention may be paid to situational and environmental variables, such as the duration and pre-requisites of an activity, as well as points of interaction with technology, as these variables may affect the performance of this activity.

Phase 3: In this phase, the individual workflows of each activity may be consolidated to form an overall global systemic workflow to capture the interrelationships between the CPs. Emphasis may be placed on extracting salient features of each activity in order to develop a system-wide engineering perspective that may be necessary for application development.

While modeling is underway, this methodology may consider the following areas during the three phases:

Tasks: After identifying and defining an activity, this activity may be decomposed into sequential or concurrent tasks that represent the steps in the activity. Relationships between tasks within an activity will also be investigated and documented. These tasks provide a detailed view of the workflow at a much finer level of granularity.

Information: For each activity, information absorbed and produced by this activity as well as its modes of collection and usage may be documented.

Communication: During the completion of an activity, communication may take place between participants in the activity. If that is the case, parameters related to this communication may be documented. Such parameters may be the means by which this communication takes place (e.g., face-to-face, email, fax, phone calls) as well as the duration of this communication.

Resources: Any activity may require resources for its completion. For instance, an activity may require the use of a software tool, dictation on a phone, recording a voice message, updating a whiteboard, scanning a document, consulting a paper chart or form. User reliability on these resources may impact significantly the requirements of an application.

Example embodiments of this invention may be implemented in a mobile phone, and more specifically in a smart phone. Current mobile phone offerings pack a very large processing power and the idea of adding computationally intensive tasks to them is not too outrageous. The complication becomes one of access to their internal workings. That is why this invention may use smart phones. Currently around thirty percent of mobile phones are smart phones and this percentage is expected to grow over time.

Current smart platforms use a Microsoft Windows, a Mac OS X, an Android, a Symbian or a Palm OS as their operating systems. All of these operating systems provide a development system for third party developers, promote access to their systems and currently have solutions that are made by third parties.

The centerpiece of this system is the integrated computing systems that implement the data storage, workflow and third party integration into an embodiment with preferred features such as security, scalability, user interface and easy access. Part of this system is referred to as the Electronic Health Record (EHR) system. Every point of integration and access between health care provider and patient introduces delay and cost to the equation and at times it is an unpredictable cost such as those incurred with interface to an insurance company.

Expansion of this concept to include modes of communication other than smart phones are available through either dedicated proxies, virtual communicators or simply a dedicated server where a phone connected via a landline or a cell phone will use its audio communication capability to transmit the voice for user authentication. Depending on the mode the problem of authentication may deviate from speaker recognition to one of voice recognition. In this case the problem is that of matching a sample audio with one stored set of templates to verify a match versus matching a sample audio with a set of stored templates to determine the closest match and then determining if the match meets an authentication criterion. Virtual or Proxy devices can easily be configured to perform a single match problem by providing a unique communication path to a single user such as assigning a phone number per user or using a code entered after making a phone connection. Layers of security may be implemented here such as encrypted codes, revolving passwords, time limited access and others to provide the continuity required for the secured access.

The method described in this specification for electronic health record management in general deals with security, biometric authentication and ease of use for not only the end user but also some sort of service providers (commercial, governmental and others). This same mechanism may be used in other modes of operation and in particular banking such as asset management, cash management, and retirement packages among others. Managing access to other personal accounts such as insurance (e.g. health, car, home, boat), employer accounts (e.g., Flexible Spending Accounts, paycheck), family and friends networks and any other mode that requires a level of security may benefit from this invention.

It should be noted that references to "an" embodiment in this disclosure are not necessarily to the same embodiment, and they mean at least one.

In this specification, "a" and "an" and similar phrases are to be interpreted as "at least one" and "one or more."

Many of the elements described in the disclosed embodiments may be implemented as modules. A module is defined here as an isolatable element that performs a defined function and has a defined interface to other elements. The modules described in this disclosure may be implemented in hardware, software, firmware, wetware (i.e hardware with a biological element) or a combination thereof, all of which are behaviorally equivalent. For example, modules may be implemented as a software routine written in a computer language (such as C, C++, Fortran, Java, Basic, Matlab or the like) or a modeling/simulation program such as Simulink, Stateflow, GNU Octave, or Lab VIEWMathScript. Additionally, it may be possible to implement modules using physical hardware that incorporates discrete or programmable analog, digital and/or quantum hardware. Examples of programmable hardware include: computers, microcontrollers, microprocessors, application-specific integrated circuits (ASICs); field programmable gate arrays (FPGAs); and complex programmable logic devices (CPLDs). Computers, microcontrollers and microprocessors are programmed using languages such as assembly, C, C++ or the like. FPGAs, ASICs and CPLDs are often programmed using hardware description languages (HDL) such as VHSIC hardware description language (VHDL) or Verilog that configure connections between internal hardware modules with lesser functionality on a programmable device. Finally, it needs to be emphasized that the above mentioned technologies are often used in combination to achieve the result of a functional module.

The disclosure of this patent document incorporates material which is subject to copyright protection. The copyright owner has no objection to the facsimile reproduction by anyone of the patent document or the patent disclosure, as it appears in the Patent and Trademark Office patent file or records, for the limited purposes required by law, but otherwise reserves all copyright rights whatsoever.

While various embodiments have been described above, it should be understood that they have been presented by way of example, and not limitation. It will be apparent to persons skilled in the relevant art(s) that various changes in form and detail can be made therein without departing from the spirit and scope. In fact, after reading the above description, it will be apparent to one skilled in the relevant art(s) how to implement alternative embodiments. Thus, the present embodiments should not be limited by any of the above described exemplary embodiments. In particular, it should be noted that, for example purposes, the above explanation has focused on the example(s) of a centralized EHR Database Server which may perform authentication tasks and stores health record. However, one skilled in the art will recognize that embodiments of the invention could be implemented in a system, in which EHR Database server tasks are implemented in a distributed system. In such a distributed system, multiple servers may perform the tasks related to the EHR Database Server.

In addition, it should be understood that any figures which highlight the functionality and advantages, are presented for example purposes only. The disclosed architecture is sufficiently flexible and configurable, such that it may be utilized in ways other than that shown. For example, the steps listed in any flowchart may be re-ordered or only optionally used in some embodiments.

Further, the purpose of the Abstract of the Disclosure is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The Abstract of the Disclosure is not intended to be limiting as to the scope in any way.

Finally, it is the applicant's intent that only claims that include the express language "means for" or "step for" be interpreted under 35 U.S.C. 112, paragraph 6. Claims that do not expressly include the phrase "means for" or "step for" are not to be interpreted under 35 U.S.C. 112, paragraph 6.

What is claimed is:

1. A method employing a portable Electronic Health Record (EHR) enabled device to perform biometric authentication of a user, comprising:
    a) storing a first decryption key on said portable EHR enabled device;
    b) receiving a request at an EHR database server from an office system, said EHR database server comprising an EHR database, said EHR database comprising a user health record;
    c) wirelessly communicating a first encrypted message from said EHR database server to said portable EHR enabled device in response to said request
    d) decrypting said first encrypted message on the portable EHR enabled device using said first decryption key, said first decrypted message including a request to perform a biometric authentication to approve a transaction between said EHR database server and an EHR Database client;
    e) said portable EHR enabled device prompting said user to speak a pass phrase and storing said spoken voice of said user;
    f) said portable EHR enabled device creating a plurality of variables, said plurality of variables are obtained by analyzing said stored spoken voice and include said pass phrase and at least one more variable characterizing said spoken voice,
    g) said portable EHR enabled device encrypting a second message using a second encryption key, said second message including a session identification information and said plurality of variables;
    h) said portable EHR enabled device wirelessly transmitting said second encrypted message to said EHR database server; and
    i) said EHR database server analyzing said plurality of variables to determine the identity of said user and to determine whether said biometric authentication is successful and said transaction is approved.

2. The method of claim 1, further comprising said EHR database server logging access to the EHR database server for tracking purposes.

3. The method of claim 1, further comprising EHR database server determining a successful biometric authentication if said session identification information, pass phrase, and speaker identity matches with the user health record data.

4. The method of claim 1, wherein said health record data includes at least one of the following:
    a) said user medical history;
    b) said user demographics;
    c) said user medical insurance;
    d) an employment status;
    e) a responsible individual; and
    f) pre-existing conditions.

5. The method of claim 1, wherein said session identification information is selected from a group consisting of:
    a) said portable EHR enabled device phone number;
    b) said portable EHR enabled device IP address;
    c) said portable EHR enabled device MAC address;
    d) said portable EHR enabled device IMSI number; and
    e) said portable EHR enabled device IMEI number.

6. The method of claim 1, wherein access to said EHR database server is available for use by said office system for a limited time period.

7. A portable Electronic Health Record (EHR) enabled device comprising:
- a processor;
- a non-transitory memory having instructions stored thereon that, in response to execution by the processor, cause the processor to perform operations comprising:
  - a) storing a first decryption key;
  - b) receiving a first encrypted message from an EHR database server, said EHR database server storing a user health record in an EHR database, said first encrypted message transmitted by said EHR database server in response to a request from an office system;
  - c) decrypting said first encrypted message using said first decryption key, said first decrypted message including a request to perform a biometric authentication to approve a transaction between said EHR database server and an EHR Database client;
  - d) prompting said user to speak a pass phrase and storing said spoken voice of said user;
  - e) creating a plurality of variables, said plurality of variables are obtained by analyzing said stored spoken voice and include said pass phrase and at least one more variable characterizing said spoken voice;
  - f) encrypting a second message using a second encryption key, said second message including a session identification information and said plurality of variables;
  - g) transmitting said second encrypted message to said EHR database server; and
  - h) receiving a determination from said EHR database server of whether said biometric authentication is successful and said transaction is approved.

8. The portable EHR enabled device of claim 7, wherein said EHR database server provides a real-time response determining whether said biometric authentication is successful.

9. The portable EHR enabled device of claim 7, wherein said session identification information is selected from a group consisting of:
- a) said portable EHR enabled device phone number;
- b) said portable EHR enabled device IP address;
- c) said portable EHR enabled device MAC address;
- d) said portable EHR enabled device IMSI number; and
- e) said portable EHR enabled device IMEI number.

* * * * *